United States Patent

Floyd et al.

[11] Patent Number: 5,849,951
[45] Date of Patent: Dec. 15, 1998

[54] SYNTHESIS OF CARBOXYLIC AND HYDROXAMIC ACID DERIVATIVES

[75] Inventors: Christopher David Floyd; Mark Whittaker, both of Oxford, United Kingdom

[73] Assignee: British Biotech Pharmaceuticals Limited, Oxford, England

[21] Appl. No.: 894,842

[22] PCT Filed: Mar. 1, 1996

[86] PCT No.: PCT/GB96/00467

§ 371 Date: Aug. 29, 1997

§ 102(e) Date: Aug. 29, 1997

[87] PCT Pub. No.: WO96/26918

PCT Pub. Date: Sep. 6, 1996

[30] Foreign Application Priority Data

Mar. 1, 1995 [GB] United Kingdom .................. 9504084

[51] Int. Cl.$^6$ ................................. C07C 229/00
[52] U.S. Cl. ........................ 562/621; 562/623; 562/442
[58] Field of Search ................... 562/621, 623, 562/442

[56] References Cited

FOREIGN PATENT DOCUMENTS

WO 95/02566  1/1995  WIPO ........................... C07B 43/06

OTHER PUBLICATIONS

UGI, 'From Isocyanides via Four Component Condensations to Antibiotic Syntheses,' Angew. Chem. Int. Ed. Engl. 21 (1982) pp. 810–819, 1982.

Primary Examiner—Gary Geist
Assistant Examiner—Brian J. Davis
Attorney, Agent, or Firm—Banner & Witcoff, Ltd.

[57] ABSTRACT

A method for the preparation of a compound of formula (I)

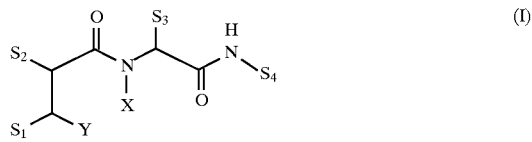

wherein X is hydrogen; Y is (i) a group —$CO_2R_5$ wherein $R_5$ is a carboxyl protecting group or (ii) a group —$CONR_6OR_7$ wherein $R_6$ is an amino protecting group and $R_7$ is a hydroxyl protecting group; and $S_1$, $S_2$, $S_3$ and $S_4$ each represent covalently bound moieties which are substantially non-reactive with the reaction components (II), (III), or (IV) defined below, which method comprises causing the co-condensation in a liquid organic medium of a carboxylic acid reaction component of formula (II); an aldehyde of formula (IIIA); ammonia; and an isonitrile reaction component of formula (IV):

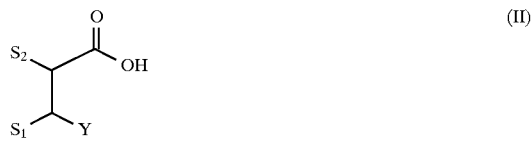

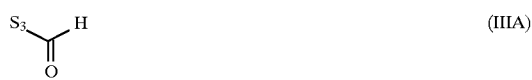

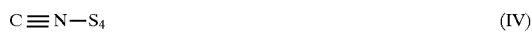

wherein Y, $S_1$, $S_2$, $S_3$ and $S_4$ are as defined with respect to formula (I).

3 Claims, No Drawings

SYNTHESIS OF CARBOXYLIC AND HYDROXAMIC ACID DERIVATIVES

The present invention relates to a method for the preparation of hydroxamic acid and carboxylic acid derivatives, particularly biologically active compounds, and especially matrix metalloproteinase inhibitors.

BACKGROUND OF THE INVENTION

Biologically Active Hydroxamic Acid and Carboxylic Acid Derivatives

Compounds which have the property of inhibiting the action of metalloproteinases involved in connective tissue breakdown such as collagenase, stromelysin and gelatinase (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. It has been found that hydroxamic acid MMP inhibitors can also inhibit the production of the cytokine tumour necrosis factor (herein referred to as "TNF") (Mohler et al., Nature, 1994, 370, 218–220; Gearing A J H et al., Nature 1994, 370. 555–557; McGeehan G M et al., Nature 1994, 370, 558–561). Compounds which inhibit the production or action of TNF are thought to be potentially useful for the treatment or prophylaxis of many inflammatory, infectious, immunological or malignant diseases. These include, but are not restricted to, septic shock, haemodynamic shock and sepsis syndrome, post ischaemic reperfusion injury, malaria, Crohn's disease, mycobacterial infection, meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury. Since excessive TNF production has been noted in several diseases or conditions also characterised by MMP-mediated tissue degradation, compounds which inhibit both MMPs and TNF production may have particular advantages in the treatment or prophylaxis of diseases or conditions in which both mechanisms are involved.

Metalloproteinases are characterised by the presence in the structure of a zinc(II) ionic site. It is now known that there exists a range of metalloproteinase enzymes that includes fibroblast collagenase (Type 1), PMN-collagenase, 72 kDa-gelatinase, 92 kDa-gelatinase, stromelysin, stromelysin-2 and PUMP-1 (J. F. Woessner, FASEB J, 1991, 5, 2145–2154). Many known MMP inhibitors are peptide derivatives, based on naturally occuring amino acids, and are analogues of the cleavage site in the collagen molecule. A recent paper by Chapman et al. (J. Med. Chem., 1993, 36, 4293–4301) reports some general structure/activity findings in a series of N-carboxyalkyl peptides. Other known MMP inhibitors are less peptidic in structure, and may more properly be viewed as pseudopeptides or peptide mimetics. Such compounds usually have a functional group capable of binding to the zinc (II) site in the MMP, and known classes include those in which the zinc binding group is a hydroxamic acid, carboxylic acid, sulphydryl, and oxygenated phosphorus (eg phosphinic acid and phosphonamidate including aminophosphonic acid) groups.

Two known classes of pseudopeptide or peptide mimetic MMP inhibitors have a hydroxamic acid group and a carboxylic group respectively as their zinc binding groups.

With a few exceptions, such known MMPs may be represented by the structural formula (A)

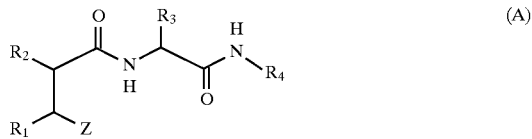

(A)

in which Z is the zinc binding hydroxamic acid (—CONHOH) or carboxylic acid (—COOH) group and the groups $R_1$ to $R_4$ are variable in accordance with the specific prior art disclosures of such compounds. Examples of patent publications disclosing such structures are given below.

The following patent publications disclose pseudopeptide hydroxamic acid-based MMP inhibitors:

U.S. Pat. No. 4,599,361 (Searle)
EP-A-0236872 (Roche)
EP-A-0274453 (Bellon)
WO 90/05716 (British Bio-technology)
WO 90105719 (British Bio-technology)
WO 91/02716 (British Bio-technology)
EP-A-0489577 (Celltech)
EP-A-0489579 (Celitech)
EP-A-0497192 (Roche)
WO 92/13831 (British Bio-technology)
WO 92/22523 (Research Corporation Technologies)
WO 93/09090 (Yamanouchi)
WO 93/09097 (Sankyo)
WO 93/20047 (British Bio-technology)
WO 93/24449 (Celltech)
WO 93/24475 (Celltech)
U.S. Pat. No. 5,256,657 (Sterling Winthrop)
EP-A-0574758 (Roche)
WO 94/02446 (British Bio-technology)
WO 94/02447 (British Bio-technology)
WO 94/21612 (Otsuka)
WO 94/25434 (Celltech)
WO 94/25435 (Celltech)

The following patent publications disclose pseudopepfide carboxylic acid-based MMP inhibitors:

EP-A-0489577 (Celltech)
EP-A-0489579 (Celltech)
WO 93/24449 (Celltech)
WO 93/24475 (Celltech)
WO 94/25434 (Celitech)
WO 94/25435 (Celltech)

A key reaction, described in the above patent applications, for the synthesis of the pseudopeptide metalloproteinase inhibitors is the coupling of a carboxylic acid derivative of formula (B) with an amino acid derivative of formula (C)

(B)

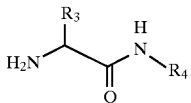

(C)

wherein $Z^1$ is a protected hydroxamic acid group or a protected carboxylic acid group to give a compound of general formula (D):

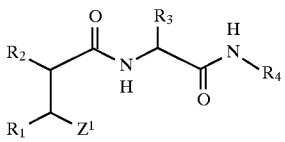

(D)

This compound (D) is then converted to a compound of general formula (A) by transformation of the group $Z^1$ to a zinc binding group Z as defined for general formula (A).

A disadvantage of this route is that the preparation of the amino acid derivative (C) usually involves a number of steps, particularly when it is an unnatural amino acid derivative, as is often desirable. There is therefore a need for alternative methods for the preparation of hydroxamic acid and carboxylic acid based compounds of type (A).

Solid Phase Synthesis

Solid phase synthesis is an established and effective method for the preparation of peptides, and offers advantages over conventional solution phase chemistry in terms of purification and simplicity (Atherton E, Sheppard R C, Solid Phase Peptide Synthesis: A Practical Approach; IRL Press at Oxford University Press: Oxford, 1989). Solid phase synthesis may also be used for the preparation of non-peptide molecules (Leznoff C C, Acc. Chem. Res., 1978, 11, 327–333) and recently there has been considerable interest in the application of this methodology to the synthesis of combinatorial libraries for biologically active lead compound optimisation and discovery (Moos W H et al., Annu. Rep. Med. Chem., 1993, 28, 315–324).

Solid phase synthesis requires an appropriate solid substrate which carries a plurality of functional groups to which the first reactive entity in the proposed synthesis may be covalently coupled, and from which the desired molecule may be cleaved after assembly. The solid substrate should be compatible with the solvents and reaction conditions that are to be used in the peptide or non-peptide synthesis.

The final step in solid phase synthesis is the cleavage of the covalent bond between the desired peptide or non-peptide molecule and the linker. It is desirable that the conditions for the cleavage are orthogonal to those used during the reactions employed for the synthesis of the peptide or non-peptide on the solid support such that undesired cleavage does not occur during the synthesis. Furthermore, the conditions for cleavage should be relatively mild such that they do not result in degradation of the desired peptide or non-peptide. Solid substrates which present hydroxyl groups as the points of attachment for the first stage of the synthesis are commonly used, for example substrates which present hydroxyl groups as derivatives of benzyl alcohol, the peptide or non-peptide being attached as a benzyl ester and cleaved by hydrolysis, acidolysis or aminolysis to release the peptide or non-peptide as a carboxylic acid, carboxylate ester or as a carboxamide. Also used are substrates which present amino groups, for example as derivatives of diphenylmethylamine, the peptide or non-peptide being attached as a carboxamide and cleaved by acidolysis to release the peptide or non-peptide as a carboxamide. Substitution of such linkers by a nitro group can enable the photolytic cleavage of the peptides or non-peptides from the residue of the solid substrate.

BRIEF DESCRIPTION OF THE INVENTION

It was the hypothesis of the present inventors that the Ugi reaction might provide an alternative route for the synthesis of pseudopeptide metalloproteinase inhibitors which could avoid the separate multi-step preparation of the amino acid derivative (C). The Ugi reaction is a four component condensation reaction between a carboxylic acid, an amine, an aldehyde and an isonitrile that proceeds to give an amino acid amide derivative (I. Ugi, Angew. Chem. Int. Ed. Engl., 1982, 21, 810–819). The reaction has been used for the synthesis of peptides (M. Waki and J. Meienhofer, J. Am. Chem. Soc., 1977, 99, 6075–6082; Ugi et al., In Chemistry and Biochemistry of Amino Acids, Peptides and Proteins, Vol. 6, Marcel Dekker New York 1982, pp 245–289) but it has found particular application for the synthesis of β-lactam derivatives (K. Kehagia et al., Tetrahedron, 1995, 51, 139–144). The inventors contemplated that such a method might be conducted in solution or with one of the components attached to a solid phase support and could find application for the manufacture of compounds of structural type (A) and in the combinatoral synthesis of a library of compounds of structural type (A).

The invention is based on the finding that compounds of type (D) which are protected precursors of compounds of structural type (A) may indeed be conveniently synthesised by application of Ugi reaction conditions, in solution or with one of the components attached to a solid phase support, for subsequent deprotection to provide the desired compounds of type (A).

DETAILED DESCRIPTION OF THE INVENTION

The present invention provides a method for the preparation of a compound of formula (I)

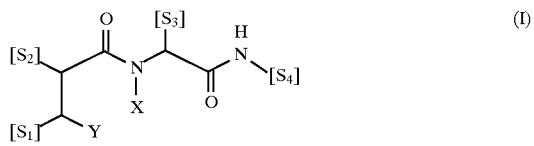

(I)

wherein

X is hydrogen or an amino protecting group, or the residue of a solid phase reaction substrate, Y is (i) a group —$CO_2R_5$ wherein $R_5$ is a carboxyl protecting group or the residue of a solid phase reaction substrate or (ii) a group —$CONR_6OR_7$ wherein $R_6$ is an amino protecting group or the residue of a solid phase reaction substrate and $R_7$ is a hydroxyl protecting group or the residue of a solid phase reaction substrate, and $[S_1]$, $[S_2]$, $[S_3]$ and $[S_4]$ each represent covalently bound moieties which are substantially non reactive with the reaction components (II), (III), or (IV) defined below, provided that only one of X, $R_5$, $R_6$ and $R_7$ is the residue of a solid phase reaction substrate, which method comprises causing the co-condensation in a liquid organic medium of three reaction components, namely a carboxylic acid reaction component of formula (II),

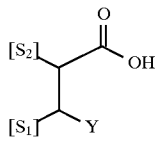
(II)

and an imine reaction component of formula (III),

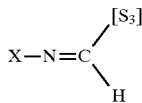
(III)

and an isonitrile reaction component of formula (IV),

C≡N—[S$_4$]  (IV)

wherein X, Y, [S$_1$], [S$_2$], [S$_3$] and [S$_4$] are as defined with respect to formula (I).

As used herein the term "amino protecting group" means a group which may be used for the protection, i.e. temporary blocking, of amino nitrogen functionality. Such groups are widely known, for example from the art of peptide synthesis, and are discussed in the widely used handbook by T. W. Greene and P. G. M. Wuts, Protective Groups in Organic Synthesis, 2nd Edition, Wiley, New York, 1991. Specific examples of amino protecting groups include allyl and benzyl or benzyl optionally substituted in the phenyl ring by one or more nitro or methoxy substituents, for example 4-methoxybenzyl or 2,4-dimethoxybenzyl.

As used herein the term "carboxylic acid protecting group" means a group which may be used for the protection, i.e. temporary blocking, of the oxygen functionality within a carboxylic acid. Again such groups are widely known, for example from the art of peptide synthesis, and are discussed in the widely used handbook by T. W. Greene and P. G. M. Wuts, Protective Groups in Organic Synthesis, 2nd Edition, Wiley, New York, 1991. Specific examples of carboxyl protecting groups include allyl, t-butyl, and benzyl or benzyl optionally substituted in the phenyl ring by one or more nitro or methoxy substituents, for example 4-methoxybenzyl or 2,4-dimethoxybenzyl.

As used herein the term "hydroxyl protecting group" means a group which may be used for the protection, i.e. temporary blocking, of the oxygen functionality of the hydroxyl group. Again such groups are widely known, for example from the art of peptide synthesis, and are discussed in the widely used handbook by T. W. Greene and P. G. M. Wuts, Protective Groups in Organic Synthesis, 2nd Edition, Wiley, New York, 1991. Specific examples of hydroxyl protecting groups include allyl, t-butyl, trimethylsilyl and benzyl or benzyl optionally substituted in the phenyl ring by one or more nitro or methoxy substituents, for example 4-methoxybenzyl or 2,4-dimethoxybenzyl.

In carrying out the above three-component co-condensation method of the invention, the imine reaction component (III) may be added to the reaction medium together with the carboxylic acid and isonitrile reaction components. It may also be preformed by the condensation of an aldehyde of formula (IIIA) and an amine of formula (IIIB):

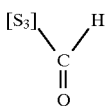
(IIIA)

X—NH$_2$  (IIIB)

wherein X and [S$_3$] are as defined with respect to formula (I), and subsequently the carboxylic acid and isonitrile reaction components may be added without isolation of the preformed imine reaction component. Note: Compounds of formula (IIIB) have been referred to as "amines". Since X in formula (IIIB) may be hydrogen, the "amine" (IIIB) may be ammonia. As used herein in relation to compounds of formula (IIIB), the term "amine" includes ammonia.

In a modification of the method of the invention, the imine reaction component (III) may be formed in situ by the condensation of an aldehyde of formula (IIIA) and an amine of formula (IIIB) as defined above. In this case, the method of the invention comprises causing the co-condensation in a liquid organic medium of four reaction components, namely the carboxylic acid reaction component of formula (II) above, the aldehyde reaction component of formula (IIIA) above, the amine reaction component of formula (IIIB) above, and the isonitrile reaction component of formula (IV) above, moieties [S$_1$], [S$_2$], [S$_3$] and [S$_4$] being substantially non reactive with these reaction components.

The three- or four-component co-condensation method of the invention may be conducted in a protic solvent such as methanol or 2,2,2-trifluoroethanol, in an aprotic solvent (e.g. tetrahydrofuran, chloroform, methylene chloride or acetonitrile) or in a mixed protic/aprotic solvent system. Methanol is the presently preferred reaction medium, but selection of appropriate organic liquid media for specific combinations of reaction components is a matter of routine. The reaction components are added to the chosen liquid reaction medium and caused to co-react. In the case where the imine is preformed, the subsequent co-condensation of carboxylic acid, imine and isonitrile components may proceed in higher yield if conducted in an aprotic solvent (e.g. tetrahydrofuran) in the presence of a Lewis acid catalyst (e.g. zinc(II) chloride).

The moieties [S$_1$], [S$_2$], [S$_3$] and [S$_4$] in the reaction components are, of course, dictated by the structure of the desired end product of the method of the invention. To minimise unwanted by-products, in their respective reaction components these moieties should not contain functional substituents which react substantially with the cognate reaction components.

In the three- and four-component methods of the invention, the co-condensation may be carried out with all reaction components in solution in the organic liquid medium; or with the carboxylic acid component (II) covalently bound to the residue of a solid phase reaction substrate, and the remaining components in solution; or with the imine component (III) covalently bound to the residue of a solid phase reaction substrate, and the remaining components in solution; or with the amino group of component (IIIB) covalently bound to the residue of a solid phase reaction substrate, and the remaining components in solution.

The term "residue of a solid substrate" as used in the definition of groups X and Y of compound (I) or reaction components (II), (III) and (IIIB) refers to a solid base substrate which is substantially insoluble in aqueous or organic reaction media and which is directly, or indirectly through suitable linker groups, linked to the relevant N or O atom by a covalent bond which is cleavable by acid hydrolysis or by photolysis.

Base substrates include those known in the art of solid phase peptide synthesis (see for example those described in Stewart J M and Young J D, Solid Phase Peptide Synthesis, 2nd Ed; Pierce Chemical Company: Rockford, Ill., 1984). They include inorganic substrates, for example kieselguhr, silica gel and controlled pore glass and polymeric organic substrates, for example polystyrene polypropylene, polyethylene glycol, polyacrylamide, cellulose, as well as composite inorganic/polymeric substrates such as polyacrylamide supported within a matrix of kieselguhr particles. Known base substrates also include amino and hydroxy functionalised solid substrates, ie those which are chemically modified by introduction of amino or hydroxyl groups, to serve as convenient points for further chemical manipulation. Examples of particular amino or hydroxy functionalised solid supports are hydroxymethyl polystyrene, benzhydrylamine polystyrene ("BHA Resin"), methyl. benzhydrylamine polystyrene ("MBHA Resin"), polyethylene glycol polystyrene ("PEG-PS"), poly(dimethylacrylamide) polystyrene composite ("Polyhipe"), polyacrylamide Kieselguhr composite ("Macrosorb") or functionalised controlled pore glass.

It is known from the art of solid phase peptide synthesis that hydroxyl- or amino-carrying linker groups can be introduced onto amino and hydroxy functionalised solid substrates, the linker group having characteristics which facilitate the cleavage of the desired synthesised molecule from the solid support. The hydroxyl or amino groups presented by the linker groups serve as points for attachment of the first reactive entity in the proposed synthesis. Thus, in case of a hydroxyl-carrying linker group, the first amino acid of the peptide to be constructed may be attached as an ester formed between the linker-presented hydroxyl group and the carboxyl group of the amino acid. In the case of amino-carrying linker groups, the first amino acid of the peptide to be constructed may be attached as a carboxamide formed between the linker-presented amino group and the carboxyl group of the amino acid. An example of a solid support resin presenting amino groups on linker groups attached to the base substrate is the resin 5-(4'-aminomethyl-3',5'-dimethoxyphenoxy)-(N4-methylbenzhydryl)pentyramide-copoly(styrene-1%-divinylbenzene) resin which has the structure

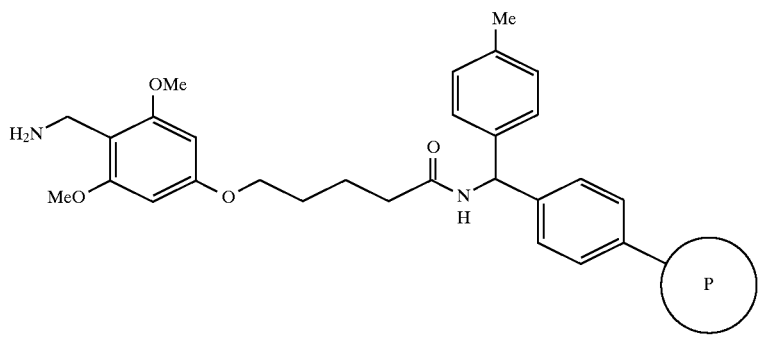

wherein "P" represents the copolystyrene divinylbenzene polymer backbone.

In the solid phase synthesis aspects of the present invention:

the carboxylic reaction component (II) may, for example, be attached to hydroxy groups presented by a solid base substrate as a carboxylic ester, or to amino groups presented by a solid base substrate as a N-alkoxycarboxamide; or the imine reaction component (III) may, for example, be formed on the amino groups presented by a solid base substrate, by reaction of such amine groups with the aldehyde component (IIIA); or the amine reaction component (IIIB) may be a solid base substrate which presents amino groups.

By analogy with the methods of solid phase peptide synthesis, in the foregoing options in which the carboxylic or imine reaction components, or the amino group of component (IIIB), are linked to the residue of a solid base substrate, the bond between the reaction component and the substrate should be cleavable, by acid hydrolysis or photolysis. In practice this is often achieved by using a substrate in which the hydroxy or amino groups forming the points of attachment in components (II) or (III), or the amino group of component (IIIB), are presented by benzylic alcohol or benzylamine derived linker groups which in turn are covalently bound to a solid base substrate. Such linker groups may, for example, have formula (V):

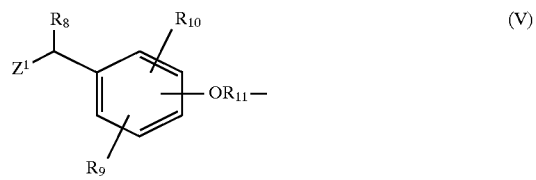

wherein $Z^1$ represents 'OH, $—NH_2$ or $—ONH_2$;

$R_8$ represents hydrogen, $C_1$–$C_6$ alkyl, or phenyl optionally substituted by one or more substituents selected from $C_1$–$C_6$ alkyl, $C_1$–$C_6$ alkoxy, halogen, nitrile or $NO_2$;

$R_9$ and $R_{10}$ independently represent hydrogen, $C_1$–$C_6$ alkyl, $C_1$–$C_6$ alkoxy, halogen, nitrite or $NO_2$;

$R_{11}$ represents a group $-(X^1)_q-Y^1-$ wherein q is 0 or 1, $X^1$ represents $—C(=O)—$, $—CH_2—$, $—CH_2C(=O)—$, $—O(CH_2)_nC(=O)-$, $—O(CH_2)_nC(=O)—(A^1)m-$, or $—O(CH_2)_nC(=O)—(A^1)m-B^1-$, wherein n is an integer from 1 to 6, m is 0 or 1, $A^1$ represents $—O—CH(R_{12})—NH—$ wherein $R_{12}$ is the side chain of a natural or unnatural alpha amino acid, $B^1$ represents a spacer group $—NH(CH_2)p-$ wherein p is 0 or an integer from 1 to 6, and Y represents $—O—$ or $—NH—$, the $R_{11}$, free valency being satisfied by covalent bonding to the solid base substrate.

Another class of linker groups has formula (VA):

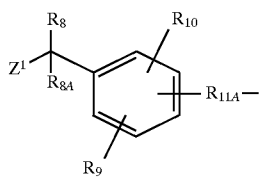

wherein $Z^1R_8$ $R_9$ and $R_{10}$ are as defined in formula (V), $R_{8A}$ is as defined for $R_8$ in formula (V), and $R_{11A}$ is a bond or is as defined for $R_{11}$ in formula (V).

The product of the method of the invention is a compound of formula (I) defined above. However that product (I) may be further treated, in one or several steps, before or after isolation from the reaction medium, to remove any amine protecting group X, or any amine protecting group, carboxyl protecting group or hydroxyl protecting group present in group Y (or indeed in moieties $[S_1], [S_2], [S_3]$ and $[S_4]$), and, in the case where one of X, $R_5$, $R_6$ and $R_7$ is the residue of a solid phase reaction substrate, to cleave the covalent bond between that substrate and the relevant N atom of X or N or O atom of Y. Following such protecting group removal, and any necessary cleavage from solid phase reaction substrate, the product has the structure (IA):

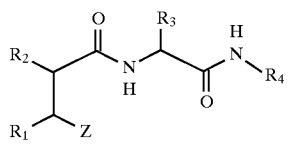

wherein Z is a carboxylic acid group —COOH or a hydroxamic acid group —CONHOH, and $R_1$–$R_4$ are either the same as $[S_1]$–$[S_4]$ or are the result of deprotection of one or more of $[S_1]$–$[S_4]$. As discussed above, under the heading "Background to the Invention" many members of the class of compounds represented by formula (IA) have valuable biological activities, particularly the ability to inhibit the activity of the matrix metalloproteinase enzymes. The method of the invention therefore finds particular application in the synthesis of matrix metalloproteinase inhibitors having the general formula (IA), many examples of which are described in the patent and other publications listed earlier.

Removal of amine protecting groups, carboxyl protecting groups or hydroxyl protecting groups as referred to in the preceeding paragraph is a common procedure requiring little or no elaboration. The art of peptide synthesis is a prolific source of detailed knowledge of these methods, as is the reference work cited earlier, namely T. W. Greene and P. G. M. Wuts, Protective Groups in Organic Synthesis, 2nd Edition. Wiley, New York, 1991.

The following Examples disclose the utility of the method of the invention for the preparation of biologically active hydroxamic acid derivatives. The carboxylic acids produced as intermediates in Examples 1–4 and as the product in Example 6 are also biologically active.

The following abbreviations have been used throughout:

| | |
|---|---|
| DCM | Dichloromethane |
| DMF | N,N-Dimethylformamide |
| EDC | N-Ethyl-N'-(3-dimethylaminopropyl)carbodiimide hydrochloride |
| HOBt | 1-Hydroxybenzotriazole |
| NMM | N-Methylmorpholine |
| TFA | Trifluoroacetic acid |
| TLC | Thin layer chromatography |

$^1$H and $^{13}$C NMR spectra were recorded using a Bruker AC 250E spectrometer at 250.1 and 62.9 MHz, respectively.

EXAMPLE 1

3R-[2,2-Dimethyl-1S,R-(benzylcarbamoyl)propylcarbamoyl]-5-methylhexano-hydroxamic acid

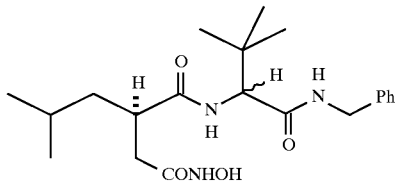

Step A
t-Butyl 3R-[2,2-dimethyl-1S,R-(benzylcarbamoyl)propyl(2,4-dimethoxybenzyl)-carbamoyl]-5-methylhexanoate Trimethylacetaldehyde (0.56 ml, 5.17 mmol) was added to a stirred solution of 2,4-dimethoxybenzylamine hydrochloride (0.86 g, 5.17 mmol) and triethylamine (0.72 ml, 5.17 mmol) in methanol (30 ml) at room temperature. To this solution was added benzyl isocyanide (0.97 ml, 5.17 mmol) followed by 2R-(2-methylpropyl)succinic acid-4-t-butyl ester (1.19 g, 5.17 mmol). The mixture was stirred for 2 h and concentrated under reduced pressure to give a pale yellow wax. The residue was taken up in DCM and washed with 1M $Na_2CO_3$, 1M HCl and brine, dried over anhydrous $MgSO_4$, filtered and evaporated. Column chromatography (Silica gel; 2:1 hexane/diethyl ether) gave the title compound (1.13 g, 38%) as a white foam. $^1$H NMR (CDCl$_3$) δ 7.25 (6H, m), 7.00 (1H, m), 6.42–6.25 (2H, m), 5.06–4.87 (2H, m), 4.63–4.32 (2H, m), 4.20 (1H, m), 3.82–3.65 (6H, br m), 3.10–2.41 (2H, br m), 2.28 (1H, m), 1.48–1.18 (12H, br m), 1.12 (9H, s), 0.99–0.75 (2H, br m), 0.75–0.45 (4H, br m).

Step B
3R-[2,2-Dimethyl-1S,R-(benzylcarbamoyl)propylcarbamoyl]-5-methylhexanoic acid t-Butyl 3R-[2,2-dimethyl-1S,R-(benzylcarbamoyl)propyl(2,4-dimethoxybenzyl)-carbamoyl]-5-methylhexanoate (0.90 g, 1.58 mmol) was taken up in a 1:1 TFA/DCM mixture (10 ml) and placed overnight in a refridgerator. It was noted that the mixture had changed colour from clear to deep purple. The solution was concentrated under reduced pressure and azeotroped with toluene to yield crude 3R-[2,2-dimethyl-1S,R-(benzylcarbamoyl)propylcarbamoyl]-5-methylhexanoic acid which was used directly in the next step. $^1$H NMR (CDCl$_3$) δ 7.72 (1H, m), 7.39–7.14 (5H, br m), 6.51 (1H, m), 4.47–4.25 (1H, br m), 4.07 (1H, m), 3.83–3.66 (1H, m), 2.72 (1H, m), 2.54 (1H, m), 2.38 (1H, m), 1.65–1.40 (1H, br m), 1.37–1.15 (1H, br m), 1.05–0.80 (15H, br m), Step C
O-Benzyl 3R-[2,2-dimethyl-1S, R-(benzylcarbamoyl)propylcarbamoyl]-5-methylhexanohydroxamic acid 3R-[2,2-Dimethyl-1S,R-(benzylcarbamoyl)propylcarbamoyl]-5-methylhexanoic acid (0.58 g, 1.54 mmol) was dissolved in dry DMF (7 ml) and treated with NMM (0.19 g, 1.85 mmol), HOBt (0.25 g, 1.85 mmol), EDC (0.35 g, 1.85 mmol) and O-benzylhydroxylamine (0.28 g, 2.31 mmol). The mixture was stirred overnight at room temperature and concentrated under reduced pressure. The residue was taken up in ethyl acetate and washed with water, 1M Na₂CO₃, 1M HCl and brine, dried over anhydrous MgSO₄, filtered and evaporated. Column chromatography (Silica gel; 0–5% methanol in DCM) gave the title compound (0.29 g, 39%). ¹H NMR (CDCl₃) δ 8.95 (1H, m), 7.45–7.10 (10H, br m), 7.00–6.68 (1H, br m), 6.50–6.25 (1H, br m), 5.01–4.75 (2H, br m), 4.50–3.95 (3H, br m), 2.94 (1H, m), 2.57–2.20 (2H, br m), 1.55 (2H, br m), 1.15 (1H, m), 1.07–0.78 (15H, br m).

Step D
3 R-[2,2-Dimethyl-1S, R-(benzylcarbamoyl) propylcarbamoyl]-5-methylhexano-hydroxamic acid A mixture of O-benzyl 3R-[2,2-dimethyl-1S,R-(benzylcarbamoyl)propylcarbamoyl]-5-methylhexanohydroxamic acid (0.25 g, 0.52 mmol) and 10% palladium on carbon (50 mg) in ethanol was stirred overnight at room temperature under an atmosphere of hydrogen. The mixture was filtered, concentrated under reduced pressure and the residue purified by column chromatography (Silica gel; 2–5% methanol in DCM) to give a 1:1 mixture of diastereoisomers of the title compound (82 mg, 40%) as a white powder: mp 165.2°–166.3° C.; ¹H-NMR (CD₃OD) δ 7.18 (5H, m), 4.13–4.38 (2H, br m), 4.05 (1H, m), 2.87 (1H, m), 2.40 (1H, dd, J 8.0, 14.7 Hz), 2.14–2.28 (1H, br m), 1.56–1.32 (2H, br m), 1.08 (1H, m), 0.92 (4.5H, s), 0.88 (4.5H, s), and 0.72–0.85 (6H, br m); ¹³C-NMR (CD₃OD) δ 177.58,177.19, 173.69, 173.60, 169.64, 169.40, 139.98, 139.89, 129.52, 128.75, 128.21, 60.09, 59.25, 44.21, 42.60, 42.44, 42.30, 40.22, 35.69, 35.26, 27.26, 27.10, 27.02, 23.74, 23.49, 22.63 and 22.22.

EXAMPLE 2
3 R-[1S, R-(Benzylcarbamoyl)-1-(1-methylcyclopropyl) methylcarbamoyl]-5-methylhexanohydroxamic acid

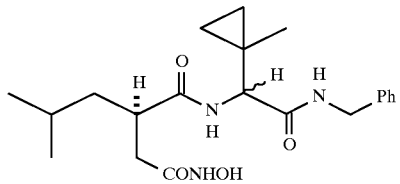

Step A
t-Butyl 3R-[1S,R-(benzylcarbamoyl)-1-(1-methylcyclopropyl)methyl(2,4-dimethoxy-benzyl) carbamoyl]-5-methylhexanoate 2,4-Dimethoxybenzylamine hydrochloride (1.68 g, 10.03 mmol) was dissolved in dry methanol containing activated 4A molecular sieves, triethylamine (1.4 ml, 10.03 mmol) and 1-methylcyclopropylaldehyde (1.2 ml, 10.94 mmol) and the mixture stirred in an ice bath for 0.5 h. To this solution was added benzyl isocyanide (1.2 ml, 10.03 mmol) followed by 2R-(2-methylpropyl)succinic acid-4-t-butyl ester (2.10 g, 9.12 mmol). The mixture was stirred overnight at room temperature, filtered and concentrated under reduced pressure. The residue was taken up in ethyl acetate and washed with water. 1M Na₂CO₃, 1M HCl and brine, dried over anhydrous MgSO₄, filtered and evaporated. Column chromatography (Silica gel; 0–5% methanol in DCM) gave the title compound (3.01 g, 59%) as a white foam. ¹H NMR (CDCl₃) δ 7.25 (6H, m), 7.03 (1H, m), 6.33 (1H, m), 4.78–3.96 (5H, br m), 3.76 (6H, m), 3.07 (1H, m), 2.45 (1H, m), 2.28 (1H, m), 1.64–1.18 (12H, br m), 1.03–0.67 (13H, br m).

Step B
3R-[1S,R-(Benzylcarbamoyl)-1-(1-methylcyclopropyl) methylcarbamoyl]-5-methylhexanoic acid t-Butyl 3R-[1S,R-(benzylcarbamoyl)-1-(1-methylcyclopropyl)methyl(2,4 -dimethoxy-benzyl) carbamoyl]-5-methylhexanoate (3.01 g, 5.40 mmol) was taken up in DCM (50 ml) and TFA (2.1 ml, 27.0 mmol) added. The mixture was left to stand at room temperature over the weekend. The solution was concentrated under reduced pressure and azeotroped with toluene and the residue was purified by column chromatography (Silica gel; 2% methanol in DCM) to give the title compound (0.63 g, 31%). ¹H NMR (CDCl₃) δ 7.55–7.03 (7H, br m), 4.48–4.21 (3H, br m), 2.76 (1H, m), 2.65 (1H, m), 2.42 (1H, m), 1.65–1.33 (2H, m), 1.19 (1H, m), 0.99–0.76 (13H, m).

Step C
3R-[1S,R-(Benzylcarbamoyl)-1-(1 -methylcyclopropyl) methylcarbamoyl]-5-methylhexanohydroxamic acid 3R-[1S,R-(Benzylcarbamoyl)-1-(1 -methylcyclopropyl) methylcarbamoyl]-5-methylhexanoic acid (0.55 g, 1.46 mmol) was dissolved in dry DMF (10 ml) and cooled in an ice bath. The solution was treated with NMM (0.22 g, 2.19 mmol), HOBt (0.24 g, 1.75 mmol), EDC (0.33 g, 1.75 mmol) and hydroxylamine hydrochloride (0.15 g, 2.19 mmol) at 0° C. and the mixture allowed to warm up to room temperature, stirred overnight and concentrated under reduced pressure. The residue was taken up in ethyl acetate and washed with water and 1M Na₂CO₃, dried over anhydrous MgSO₄, filtered and evaporated. Column chromatography (acid washed silica gel; methanol in DCM) gave the title compound (0.14 g, 25%) as a white solid. mp 175°–180° C. ¹H-NMR (CD₃OD) δ 7.06–7.24 (5H, m), 4.38–4.05 (3H, br m), 2.78 (1 H. m). 2.21 (1H, m), 2.05 (1H, m). 1.77 (1H, m), 1.55 –1.25 (3H, br m), 1.12–0.96 (2H, br m), and 0.89–0.71 (12H, m); ¹³C-NMR (CD₃OD) δ 177.33, 173.33, 173.64, 170.54, 139.84, 129.51, 129.34, 128.62, 128.21, 127.94, 59.32, 58.65, 44.02, 42.52. 42.16, 42.09, 38.29, 37.78, 37.06, 27.23, 26.97, 25.96, 23.63, 22.42, 15.89, 15.16. 11.82 and 11.19.

EXAMPLE 3
3R-[2,2-Dimethyl-1S,R-(t-butylcarbamoyl) propylcarbamoyl]-5-methylhexano-hydroxamic acid

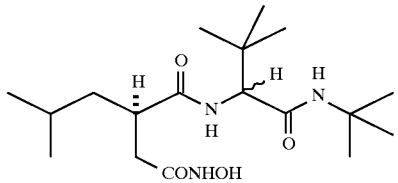

Step A
t-Butyl 3R-[2,2-dimethyl-1S,R-(t-butylcarbamoyl)propyl-carbamoyl]-5-methylhexanoate Trimethylacetaldehyde (0.24 ml, 2.17 mmol) was added to a stirred 0.2M solution of ammonia in methanol (21.7 ml, 4.34 mmol) at room temperature. After 10 min, t-butyl isocyanide (0.25 ml, 2.17 mmol) was added followed by 2R-(2-methylpropyl)succinic acid-4-t-butyl ester (0.50 g, 2.17 mmol). The mixture was stirred overnight and concentrated under reduced pressure to give t-butyl 3R-[2,2-dimethyl-1S,R-(t-butylcarbamoyl)propyl-carbamoyl]-5-methylhexanoate as an amorphous white solid (0.49 g 57%). ¹H NMR (CDCl₃) δ 6.52 (1H, d, J 9 Hz), 6.23 (1H, d, J 12 Hz), 4.20 (1H, dd, J 9.3, 6.2 Hz), 2.78–2.22 (3H, m), 1.72–1.50 (2H, m), 1.42 (4.5H, s), 1.41 (4.5H, s), 1.33 (4.5H, s),1.32 (4.5H, s), 1.30–1.05 (1H, m), 0.97 (4.5H, s), 0.96 (4.5H, s), 0.95–0.83 (6H, m).

Step B
3R-[2,2-Dimethyl-1S,R-(t-butylcarbamoyl) propylcarbamoyl]-5-methylhexanoic acid A 1:1 TFA/DCM mixture (20 ml) was added to t-butyl 3R-[2,2-dimethyl-1S,R-(t-butylcarbamoyl)propyl-carbamoyl]-5-methylhexanoate (0.49 g, 1.23 mmol) and the resulting solution placed in a refridgerator for 48 h. The solution was concentrated under reduced pressure and azeotroped with diethyl ether to yield crude 3R-[2,2-dimethyl-1S,R-(t-butylcarbamoyl)propylcarbamoyl]-5-methylhexanoic acid which was used directly in the next step. $^1$H NMR (CDCl$_3$) δ 8.98 (1H, br s), 8.11 (0.5H, d, J 9 Hz), 7.86 (0.5H, d, J 9 Hz), 6.41 (1H, d, J 16 Hz), 4.31 (1H, d, J 9 Hz), 3.03–2.35 (3H, m), 1.70–1.40 (3H, m), 1.35 (4.5H, s), 1.34 (4.5H, s), 0.98 (4.5H, s), 0.95 (4.5H, s), 0.93–0.83 (6H, m).

Step C
O-Benzyl 3R-[2,2-dimethyl-1S,R-(t-butylcarbamoyl) propylcarbamoyl]-5-methylhexanohydroxamic acid Crude 3R-[2,2-dimethyl-1S,R-(t-butylcarbamoyl) propylcarbamoyl]-5-methylhexanoic acid from the previous step was dissolved in dry DMF (20 ml) cooled to 0° C. and treated with HOBt (0.18 g, 1.36 mmol), EDC (0.29 g, 1.49 mmol) and O-benzylhydroxylamine (0.18 g, 1.49 mmol). The mixture was stirred overnight at room temperature and concentrated under reduced pressure. The residue was taken up in DCM (30 ml). An insoluble solid formed which was removed by filtration and set aside. The organics were washed with 1M HCl, 1M Na$_2$CO$_3$, and brine, dried over anhydrous MgSO$_4$, filtered and evaporated. The solid residue was combined with the previously isolated solid and crystallised from ethyl acetate (30 ml) to give O-benzyl 3R-[2,2-dimethyl-1S,R-(t-butylcarbamoyl) propylcarbamoyl]-5-methylhexanohydroxamic acid (0.27g, 49%) as a white solid. $^1$H NMR (CDCl$_3$) δ 7.35–7.20 (5H, m), 4.70 (2H, s), 4.13–3.98 (1H, m), 2.95–2.73 (1H, m), 2.28–1.95 (2H, m), 1.53–1.33 (2H, m), 1.23 (9H, s), 1.15–1.00 (1H, m), 0.93 (9H, s), 0.88–0.75 (6H, m).

Step D
3R-[2,2-Dimethyl-1S,R-(t-butylcarbamoyl) propylcarbamoyl]-5-methylhexano-hydroxamic acid A mixture of O-benzyl 3R-[2,2-dimethyl-1S, R-(t-butylcarbamoyl)propylcarbamoyl]-5-methylhexanohydroxamic acid (0.27 g, 0.60 mmol) and 10% palladium on carbon (45 mg) in ethanol (30 ml) was stirred overnight at room temperature under an atmosphere of hydrogen. The mixture was filtered, concentrated under reduced pressure to give 3R-[2,2-dimethyl-1S,R-(t-butylcarbamoyl)propylcarbamoyl]-5-methylhexano-hydroxamic acid (193 mg, 91%) as a 1:1 mixture of diastereoisomers: Off-white powder: $^1$H-NMR (CD$_3$OD) δ 7.60 (0.5H, d, J 8.7 Hz), 7.52 (0.5H, d, J 9.2 Hz), 7.35 (1H, d, J 16.7 Hz), 4.06 (1H, dd, J 15.5, 9.1 Hz), 2.83 (1H, m), 2.19 (1H, m), 2.05 (1H, m), 1.56–1.31 (2H, br m), 1.22 (4.5H, s), 1.21 (4.5H, s), 1.16–1.02 (1H, m), 0.90 (4.5H, s), 0.88 (4.5H, s), 0.88–0.73 (6H, br m); $^{13}$C-NMR (CD$_3$OD) δ 178.31, 178.19, 173.14, 171.86, 64.11, 63.53, 53.56, 43.92, 43.58, 43.52, 43.43, 38.55, 38.42, 36.70, 36.42, 30.30, 30.22, 28.76, 28.60, 28.48, 25.14, 25.06, 23.93, 23.55.

EXAMPLE 4

Synthesis of a combinatorial array of matrix metalloproteinase inhibitors

The compounds of Example 4 as set out in Array 1 below were prepared following an analogous procedure to that employed above for the synthesis of the compound of Example 3 using the appropriate 2-(substituted)succinic acid-4-t-butyl ester derivative in lieu of 2R-(2-methylpropyl)succinic acid-4-t-butyl ester, trimethylacetaldehyde and an isonitrile chosen from n-butyl isocyanide, isopropyl isocyanide, t-butyl isocyanide or cyclohexyl isocyanide. In the case of compounds 4s-4u O-tritylhydroxylamine was used in lieu of O-benzylhydroxylamine and the final hydroxamic acids were obtained by deprotection with 25% TFA in DCM. The desired hydroxamic acids were separated from the released triphenylmethane by flash separation on silica.

Array 1: Compounds of Example 4

| $R_1/R_2$ | $R_4$ = -nBu | $R_4$ = -iPr | $R_4$ = -tbu | $R_4$ = $-C_6H_{11}$ |
|---|---|---|---|---|
| $R_1$ = H— $R_2$ = Me— | NA | NA | Compound 4a | NA |
| $R_1$ = H— $R_2$ = Et-— | NA | NA | Compound 4b | NA |
| $R_1$ = H— $R_2$ = nBu- | NA | NA | Compound 4c | NA |
| $R_1$ = H— $R_2$ = $C_6H_{13}$— | Compound 4d | Compound 4e | Compound 4f | Compound 4g |
| $R_1$ = H— $R_2$ = $C_7H_{15}$— | Compound 4h | Compound 4i | Compound 4j | Compound 4k |
| $R_1$ = H— $R_2$ = $C_8H_{17}$— | Compound 4l | Compound 4m | Compound 4n | Compound 4o |
| $R_1$ = H— $R_2$ = PhCH$_2$— | NA | NA | Compound 4p | NA |
| $R_1$ = H— $R_2$ = 3-thienylCH$_2$— | Compound 4q | NA | NA | NA |

-continued

[Structure: R2-CH(H)-C(=O)-NH-CH(C(CH3)3)-C(=O)-NH-R4, with R1-CH-CONHOH branch]

| $R_1/R_2$ | $R_4$ | | | |
|---|---|---|---|---|
| | $R_4$ = -nBu | $R_4$ = -iPr | $R_4$ = -tbu | $R_4$ = $-C_6H_{11}$ |
| $R_1$ = H—<br>$R_2$ = 3,4-$(CH_2)O_2C_5H_3CH_2$— | NA | NA | Compound 4r | NA |
| $R_1$ = $CH_2$=$CHCH_2$—<br>$R_2$ = $iPrCH_2$— | Compound 4s | Compound 4t | NA | Compound 4u |
| $R_1$ = H—<br>$R_2$ = $C_{16}H_{33}$— | Compound 4v | NA | NA | Compound 4x |

Note:
It was considered unnecessary to prepare all compounds in the array in order to obtain satisfactory diversity; the term "NA" indicates those compounds whose synthesis was not attempted.

Data for the compounds of Example 4 are as follows (yields are given for over the four reaction steps):

Compound 4a: 3R-[2,2-dimethyl-1S,R-(t-butylcarbamoyl)propylcarbamoyl]-butanohydroxamic acid (1:1 mixture of diastereoisomers)

Off-white powder (28%): $^1$H-NMR ($CD_3OD$) δ 7.43 (0.5H, s), 7.38 (0.5H, s), 4.06 (0.5H, s), 4.04 (0.5H, s), 2.90–2.76 (1H, m), 2.37–2.20 (1H, m), 2.10–1.96 (1H, m), 1.22 (9H, br s), 1.05 (1.5H, d J 7.1 Hz), 1.01 (1.5H, d, J 7.0 Hz), 0.88 (9H, br s). $\upsilon_{max}$/cm (KBr) 1639.

Compound 4b: 3R-[2,2-dimethyl-1S,R-(t-butylcarbamoyl)propyl-carbamoyl]-pentanohydroxamic acid (1:1 mixture of diastereoisomers)

Off-white powder (32%): $^1$H-NMR ($CD_3OD$) δ 4.09 (0.5H, s), 4.02 (0.5H, s), 2.74–2.60 (1H, m), 2.32–2.19 (1H, m), 2.17–2.01 (1H, m), 1.60–1.30 (2H, m), 1.23 (4.5H, s), 1.21 (4.5H, s), 0.90 (4.5H, s), 0.89 (4.5H, s), 0.82 (1.5H, t, J 7.3 Hz), 0.77 (1.5H, t, J 7.4 Hz). $\upsilon_{max}$/cm (KBr) 1637.

Compound 4c: 3R-[2,2-dimethyl-1S,R-(t-butylcarbamoyl)propylcarbamoyl]-heptanohydroxamic acid (1:1 mixture of diastereoisomers)

White powder (36%): $^1$H-NMR ($CD_3OD$) δ 7.39 (0.5H, s), 7.32 (0.5H, s), 4.08 (0.5H, s), 4.02 (0.5H, s), 2.80–2.70 (1H, m), 2.32–2.19 (1H, m), 2.18–2.00 (1H, m), 1.60–1.04 (6H, m), 1.22 (4.5H, s), 1.21 (4.5H, s), 0.90 (4.5H, s), 0.87 (4.5H, s), 0.76 (3H, m). $\upsilon_{max}$/cm (KBr) 1637.

Compound 4d: 3R-[2,2-dimethyl-1S,R-(n-butylcarbamoyl)propylcarbamoyl]-nonanohydroxamic acid (1:1 mixture of diastereoisomers)

Off-white solid (9%): 1H-NMR ($CD_3OD$) δ 4.13–3.98 (1H, m), 2.78–2.67 (2H, m), 2.12–2.02 (1H, m), 2.38–2.20 (2H, m), 1.44–1.11 (14H, br m), 0.92 (4.5H, s) 0.89 (4.5H, s), 0.85–0.77 (6H, m).

Compound 4e: 3R-[2,2-dimethyl-1S,R-(i-propylcarbamoyl)propylcarbamoyl]-nonanohydroxamic acid (1:1 mixture of diastereoisomers)

Off-white solid (22%): $^1$H-NMR ($CD_3OD$) δ 4.06 (0.5H, s), 4.14 (0.5H, s), 3.92–3.79 (1H, m), 2.80–2.62 (1H, m), 2.32–2.19 (1H, m), 2.15–2.01 (1H, m), 1.50–1.14 (10H, br m), 1.06–1.01 (6H, m), 0.91 (4.5H, s), 0.88 (4.5H, s), 0.83–0.75 (3H, m).

Compound 4f: 3R-[2,2-dimethyl-1S,R-(t-butylcarbamoyl)propylcarbamoyl]-nonanohydroxamic acid (1:1 mixture of diastereoisomers)

Off-white solid (12%):$^1$H-NMR ($CD_3OD$) δ 4.09 (0.5H, s), 4.02 (0.5H, s), 2.75–2.69 (1H, m), 2.29–2.19 (1H, m), 2.11–2.02 (1H, m), 1.57–1.30 (2H, br m), 1.23 (4.5H, s), 1.22 (4.5H, s), 1.18–1.16 (8H, m), 0.90 (4.5H, s), 0.89 (4.5H, s), 0.80–0.74 (3H, m).

Compound 4g: 3R-[2,2-dimethyl-1S,R-(cyclohexylcarbamoyl)propylcarbamoyl]-nonanohydroxamic acid (1:1 mixture of diastereoisomers)

White solid (28%): $^1$H-NMR ($CD_3OD$) δ 4.13–4.06 (0.5H, m), 4.19–4.15 (0.5H, m), 3.54–3.49 (1H, m), 2.76–2.71 (1H, m), 2.12–2.00 (1H, m), 2.31–2.19 (1H, 1.80–1.40 (2H, br. m), 1.32–1.04 (18H, m), 0.90 (4.5H, s), 0.88 (4.5H, s), 0.86–0.77 (3H, m).

Compound 4h: 3R-[2,2-dimethyl-1S,R-(n-butylcarbamoyl)propylcarbamoyl]-decanohydroxamic acid (1:1 mixture of diastereoisomers)

Colourless oil (8%): $^1$H-NMR ($CD_3OD$) δ 4.07 (0.5H, s), 4.14 (0.5H, s), 2.79–2.67 (2H, m), 2.34–2.18 (2H, br m), 2.11–2.05 (1H, m), 1.47–1.16 (16H, br m), 0.93–0.89 (9H, m), 0.84–0.75 (6H, m).

Compound 4i: 3R-[2.2-dimethyl-1S,R-(i-propylcarbamoyl)propylcarbamoyl]-decanohydroxamic acid (1:1 mixture of diastereoisomers)

Yellow-brown solid (41%): $^1$H-NMR ($CD_3OD$) δ 4.19–4.06 (1H, m), 3.93–3.81 (1H, m), 2.82–2.69 (1H, m), 2.38–2.02 (2H, br m), 1.59–1.00 (18H, br m), 0.91 (4.5H, s), 0.88 (4.5H, s), 0.86–0.75 (3H, m).

Compound 4j: 3R-[2.2-dimethyl-1S,R-(t-butylcarbamoyl)propylcarbamoyl]-decanohydroxamic acid (1:1 mixture of diastereoisomers)

White solid (27%): $^1$H-NMR ($CD_3OD$) δ 4.12–4.09 (0.5H, m), 4.06–4.03 (0.5H, m), 2.79–2.68 (1H, m), 2.29–2.19 (1H, m), 2.12–2.03 (1H, m), 1.55–1.37 (2H, m), 1.22 (9H, s), 1.18–1.11 (10H, m), 0.90 (4.5H, s), 0.88 (4.5H, s), 0.79–0.75 (3H, m).

Compound 4k: 3R-[2,2-dimethyl-1S,R-(cyclohexylcarbamoyl)propylcarbamoyl]-decanohydroxamic acid (1:1 mixture of diastereoisomers)

Off-white solid (38%): $^1$H-NMR ($CD_3OD$) δ 4.22–4.18 (1H, m), 3.62–3.46 (1H, m), 2.82–2.66 (1H, m), 2.53–2.00 (2H, br m), 1.80–1.40 (2H, br m), 1.32–1.12 (20H, br m), 0.92 (4.5H, s), 0.84 (4.5H, s), 0.58 (3H, m).

Compound 4l: 3R-[2,2-dimethyl-1S,R-(n-butylcarbamoyl)propylcarbamoyl]-undecanohydroxamic acid (1:1 mixture of diastereoisomers)

Pale yellow solid (42%): ¹H-NMR (CD₃OD) δ 4.10–4.07 (0.5H, m), 4.21–4.15 (0.5H, m), 3.10–3.01 (2H, m), 2.80–2.71 (1H, m), 2.32–1.88 (2H, br m), 1.69–1.17 (18H, br m), 0.92 (3H, s), 0.88 (6H, s), 0.86–0.76 (6H, m).

Compound 4m: 3R-[2,2-dimethyl-1 S,R-(i-propylcarbamoyl)propylcarbamoyl]-undecanohydroxamic acid (3:2 mixture of diastereoisomers)

Yellow solid (45%): ¹H-NMR (CD₃OD) δ 4.22–3.99 (1H, m), 4.92–3.79 (1H, m), 2.80–2.64 (1H, m), 2.35–2.16 (1H, br m), 2.10–1.91 (1H, br m), 1.55–1.40 (2H, m), 1.26–1.00 (18H, br m), 0.93 (3H, s), 0.88 (6H, s), 0.75–0.83 (3H, m).

Compound 4n: 3R-[2,2-dimethyl-1S,R-(t-butylcarbamoyl)propylcarbamoyl]-undecanohydroxamic acid (3:2 mixture of diastereoisomers)

Pale yellow solid (10%): ¹H-NMR (CD₃OD) δ 4.12–3.97 (1H, m), 2.80–2.71 (1H, m), 2.30–2.13 (1H, m). 2.11–2.00 (1H, m), 1.51–1.47 (2H, m), 1.22 (4.5H, s), 1.20 (4.5H, s), 1.17–1.13 (12H, m), 0.90–0.88 (9H, m), 0.86–0.75 (3H, m).

Compound 4o: 3R-[2,2-dimethyl-1S,R-(cyclohexylcarbamoyl)propylcarbamoyl]-undecanohydroxamic acid (1:1 mixture of diastereoisomers)

Pale yellow solid (43%): ¹H-NMR (CD₃OD) δ 4.16–4.12 (0.5H, m). 4.06 (0.5H, m), 3.54–3.49 (1H, m). 2.78–2.71 (1H, m), 2.30–2.19 (1H, br m), 2.16–1.97 (1H, br m). 1.78–1.50 (2H. br m). 1.24–1.04 (22H, m), 0.91 (4.5H, s), 0.88 (4.5H, s), 0.86–0.76 (3H, m).

Compound 4p: 3R-[2.2-dimethyl-1S,R-(t-butylcarbamoyl)-propyl-carbamoyl]-4-phenylbutanohydroxamic acid (2:1 mixture of diastereoisomers)

Off-white powder (36%): ¹H-NMR (CD₃OD) δ 7.20–7.00 (5H, m), 4.01 (0.66H, s), 3.82 (0.33H, s), 3.16–3.00 (1H, m), 2.90–2.53 (2H, m), 2.38–2.02 (2H, m), 1.21 (3H, s), 1.17 (6H, s), 0.84 (6H, s), 0.63 (3H, s); $\nu_{max}$/cm (KBr) 1635.

Compound 4q: 3R-[2.2-dimethyl-1S, R-(n-butylcarbamoyl)-propyl-carbamoyl]-4-thien-3-ylbutanohydroxamic acid (4:1 mixture of diastereoisomers)

Brown wax (8%): ¹H-NMR (CD₃OD—CDCl₃) δ 7.52–6.82 (~7H, m), 4.34 and 4.13 (1H, dd), 3.33–3.12 (4H, m), 2.93–2.48 (3H, m), 1.52–1.32 (4H, m), 1.28 and 1.22 (~9H, s), 0.91 (3H, t).

Compound 4r: 3R-[2,2-dimethyl-1S,R-(t-butylcarbamoyl)-propyl-carbamoyl]-4-(3,4-methylenedioxyphenyl)butanohydroxamic acid (3:2 mixture of diastereoisomers)

Light brown flakes (34%): ¹H-NMR (CD₃OD) δ 6.72–6.45 (3H, m), 5.92 (1 H, s), 5.85 (1H, m), 4.12–4.20 (1H, m), 3.33–2.32 (5H, m), 1.35 (6H, s), 1.32 (3H, s), 1.21 (6H, s), 0.96 (3H); $\nu_{max}$/cm (KBr) 1640.

Compound 4s: 3R-[2,2-dimethyl-1S,R-(n-butylcarbamoyl)propylcarbamoyl]-5-methyl-2S-propen-2-yl-hexanohydroxamic acid (1:1 mixture of diastereoisomers)

Off-white amorphous solid (31%): ¹H-NMR (CDCl₃—CD₃OD) δ 5.72 (1H, m), 5.12 (2H, m), 4.41 (1H, m), 4.01 (2H, m), 3.55 (1H, m), 3.43–3.14 (3H, m), 3.02–2.52 (3H, m), 1.78–1.32 (7H, m), 1.28 and 1.22 (9H, m), 0.92 (3H, m), 0.82 (6H, m).

Compound 4t: 3R-[2,2-dimethyl-1S,R-(i-propylcarbamoyl)propylcarbamoyl]-5-methyl-2S-propen-2-yl-hexanohydroxamic acid (2:1 mixture of diastereoisomers)

Off-white amorphous solid (51%): ¹H-NMR (CDCl₃—CD₃OD) δ 5.72 (1H, m), 5.27–4.98 (2H, m), 4.48 (1H, m), 4.07 (1H, heptet), 3.33–3.12 (2H, m), 2.83–2.48 (2H, m), 1.62–1.51 (1H, m), 1.33 and 1.28 (9H, 2s), 1.33 (2H, m), 1.08–0.82 (12H, m).

Compound 4u: 3R-[2,2-dimethyl-1S,R-(cyclohexylcarbamoyl)propylcarbamoyl]-5-methyl-2S-propen-2-yl-hexanohydroxamic acid (3:1 mixture of diastereoisomers)

Light brown amorphous solid (42%): ¹H-NMR (CD₃OD) δ 5.62 (1H, m), 5.24–5.03 (2H, m), 4.45 (1H, m), 3.74 (1H, m), 3.21 (1H, m), 2.80–2.24 (3H,m), 1.94–1.51 (6H, m), 1.43 and 1.24 (~10H, 2s), 1.48–1.22 (4H, m), 1.02 (6H, m), 0.91 (6H, m).

Compound 4v: 3R-[2,2-dimethyl-1S,R-(n-butylcarbamoyl)propylcarbamoyl]-nonadecanohydroxamic acid (3:1 mixture of diastereoisomers)

Light brown glass (21%): ¹H-NMR (CD₃OD—CDCl₃) δ 7.21 (2H, m), 4.30–4.11 (1H, m), 3.55 (2H, m), 3.25–3.1 (2H, m), 2.72–2.22 (2H, m), 1.62–1.45 (2H, m), 1.32–1.12 (~39H, br m), 0.85 (3H, t), 0.72 (3H, t).

Compound 4x: 3R-[2,2-dimethyl-1S,R-(cyclohexylcarbamoyl)propylcarbamoyl]-nonadecanohydroxamic acid (3:2 mixture of diastereoisomers)

Off-white needles (23%): ¹H-NMR (CD₃OD) δ 6.61 (1H, br m), 4.74.6 (1H, br m), 4.224.10 (1H, m), 3.72–3.61 (2H, m), 2.82–2.61 (2H, m), 2.41 (1H, m), 1.93–1.55 (5H, m), 1.38–1.21 (~41H, brs), 1.02 (4H, m), 0.82 (3H, t); $\nu_{max}$/cm (KBr) 1638.

EXAMPLE 5

2S-Hydroxy-3R-(1 S R-[tert-butylcarbamoyl]-2,2-dimethyl-propylcarbamoyl)-5-methyl-hexanohydroxamic acid

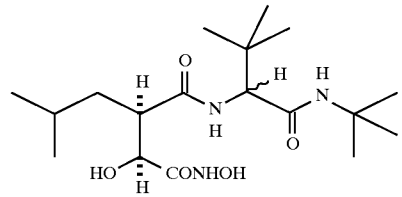

Step A

Nα-[2R-(2,2-Dimethyl-4-oxo-1,3-dioxalan-5S-yl)-4-methylpentanoyl]-D, L-tert-leucine-N-tert-butylamide Trimethylacetaldehyde (0.12 ml, 1.10 mmol) was added to a stirred 0.2M solution of ammonia in methanol (5.5 ml, 1.10 mmol) at room temperature under argon. After 1 h, t-butyl isocyanide (0.12 ml, 1.10 mmol) was added followed by 2R-(2,2-dimethyl- 4-oxo-1,3-dioxalan-5S-yl)-4-methylpentanoic acid (prepared as described in patent application WO 94/02446) (0.31 g, 1.10 mmol). The mixture was stirred for 48 h and concentrated under reduced pressure. The residue was taken up in ethyl acetate, washed with 1M aqueous sodium bicarbonate, 1M hydrochloric acid and brine, dried over anhydrous magnesium sulphate, filtered and evaporated under reduced pressure to give Nα-[2R-(2, 2-dimethyl-4-oxo-1,3-dioxalan-5S-yl)-4-methylpentanoyl]-D,L-tert-leucine-N-tert-butylamide (1:1 mixture of diastereoisomers) as a white solid (0.30 g, 77%). ¹H NMR (CDCl₃) δ 6.61 (0.5H, br s), 6.58 (0.5H, br s), 6.22 (0.5H, br s), 6.09 (0.5H, br s), 4.43 (0.5H, d, J 6.7 Hz), 4.41 (0.5H, d, J 6.7 Hz), 4.24 (0.5H, d, J 9.0 Hz), 4.17 (0.5H, d, J 9.3 Hz), 2.70 (1H, m), 1.80–1.20 (3H, m), 1.61 (1.5H, s), 1.59 (1.5H, s), 1.51 (1.5H, s), 1.49 (1.5H, s), 1.33 (4.5H, s), 1.32 (4.5H, s), 0.98(9H, s), 0.96–0.88 (6H, m).

Step B
2S-Hydroxy-3R-(1 SR-[tert-butylcarbamoyl]-2,2-dimethyl-propylcarbamoyl)-5-methyl-hexanohydroxamic acid Sodium methoxide (0.12 g, 2.24 mmol) was added to a stirred solution of hydroxylamine hydrochloride (0.16 g, 2.24 mmol) in methanol (10 ml) at room temperature. After 2 h the mixture was filtered, the filtrate cooled in an ice bath and added to a cooled solution of $N^\alpha$-[2R-(2,2-dimethyl-4-oxo-1,3-dioxalan-5S-yl)-4-methylpentanoyl]-D,L-tert-leucine-N-tert-butylamide (0.20, 0.56 mmol) in methanol (2 ml). The mixture was allowed to warm to room temperature and stirred over night. The solvent was removed under reduced pressure and the residue triturated with diethyl ether (20 ml) to give 2S-hydroxy-3R-(1 SR-[tert-butylcarbamoyl]-2,2-dimethyl-propylcarbamoyl)-5-methyl-hexanohyroxamic acid (0.102 g, 48%) (1:1 mixture of diastereoisomers) as a white powder. $^1$H-NMR (CD$_3$OD) δ 8.32 (1H, s), 4.10 (0.5H, s), 4.02 (0.5H, s), 3.93 (0.5H, d, J 6.4 Hz), 3.90 (0.5H, d, J 7.2 Hz), 2.75 (1H, m), 1.61–1.33 (2H, br m). 1.22 (4.5H, s), 1.21 (4.5H, s), 1.07 (1H, m), 0.91 (4.5H, s), 0.89 (4.5H, s), 0.79 (6H, m).

EXAMPLE 6
3R-[S,R-(t-Butylcarbamoyl-4-methylphenylmethyl) carbamoyl]-5methylhexanoic acid (3:2 mixture of diastereomers)

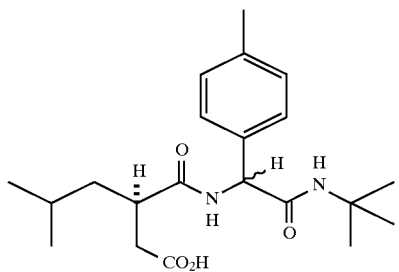

A solution (5 ml) of 25% piperidine in DMF was added to fluorenylmethyl oxycarbonyl-PAL-polystyrene (140 mg, 3 mmol/g loading, 0.042 mmol) and the resin gently agitated in the solution for 30 minutes. The resin was then drained and washed successively with DMF, DCM, 1:1 DCM and methanol (3 cycles), DCM and finally with diethyl ether. After drying in vacuo for 3 h at room temperature a solution of tolualdehyde in trimethylorthoformate (5 ml of a 1M solution) was added and the resulting resin suspension was mixed together for 3 h. The solution was drained from the resin as above and the resin washed thoroughly with DCM. The resin was then swelled in DCM (1.5 ml) and tolualdehyde (49 μL, 0.42mmol) added. After 1 h 2R-isobutylsuccinic acid-4-t-butyl ester (64 mg, 0.21 mmol) in methanol (1 ml) and t-butylisonitrile (32 μL, 0.21 mmol) were added and the whole mixture agitated together for three days. The solvents were then removed and the resin washed and dried as above. The resin was then reswelled in DCM (0.5 ml) and TFA (2 ml) and triethylsilane (100 μL) were added. After 2 h the TFA solution was collected and the resin washed with a further portion (2 ml) of TFA. The combined TFA extracts were evaporated to leave crude 3R-[S,R-(t-butylcarbamoyl-4-methylphenylmethyl)-carbamoyl]-5 methylhexanoic acid (3:2 mixture of diastereomers) as a pale solid (11 mg). $^1$H NMR (CDCl$_3$) δ 7.95 and 7.7 (~2H, m), 7.73–7.08 (~4H, m), 6.32–6.21 (1H, m), 5.17–5.05 (1H, m), 2.89–2.44 (3H, m), 2.39 and 2.32 (3H, 2s), 1.55–1.48 (3H, m), 1.33 and 1.23 (9H, 2s), 1.02–0.82 (6H, m).

We claim:
1. A method for the preparation of a compound of formula (I)

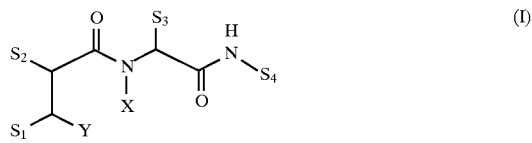

wherein

X is hydrogen,

Y is (i) a group —CO$_2$R$_5$ wherein R$_5$ is a carboxyl protecting group or (ii) a group —CONR$_6$OR$_7$ wherein R$_6$ is an amino protecting group and R$_7$ is a hydroxyl protecting group, and S$_1$, S$_2$, S$_3$ and S$_4$ each represent covalently bound moieties which are substantially non-reactive with the reaction components (II), (III), or (IV) defined below, which method comprises causing the co-condensation in a liquid organic medium of a carboxylic acid reaction component of formula (II):

an aldehyde of formula (IIA):

ammonia, and an isonitrile reaction component of formula (IV),

wherein Y, S$_1$, S$_2$, S$_3$ and S$_4$ are as defined with respect to formula (I).

2. A process as claimed in claim 1 wherein the aldehyde of formula (IIIA) is trimethylacetaldehyde.

3. A method for the preparation of a compound of formula (IA):

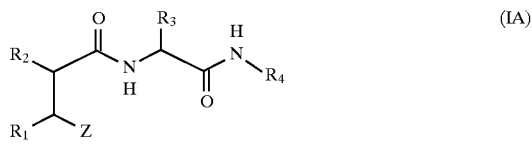

wherein Z is a carboxylic acid group —COOH or a hydroxamic acid group —CONHOH, and R$_1$–R$_4$ are the same as S$_1$–S$_4$ as defined in connection with formula (I) in claim 1, which process comprises preparing a compound of formula (1) by a process as claimed in claim 1 or claim 2, and performing the additional step of removing any amino- or carboxyl-protecting group from Y in the compound of formula (I).

* * * * *